(12) United States Patent
Liu et al.

(10) Patent No.: US 8,815,600 B2
(45) Date of Patent: Aug. 26, 2014

(54) HOMOLOGOUS RECOMBINATION-BASED DNA CLONING METHODS AND COMPOSITIONS

(75) Inventors: Weiqiang Liu, Nanjing (CN); Ping Yang, Princeton, NJ (US); Tao Wang, Nanjing (CN); Zhuying Wang, Monmouth Junction, NJ (US); Wenzhu Chen, Nanjing (CN); Fang Liang Zhang, Fanwood, NJ (US)

(73) Assignee: GenScript Hongkong, Hong Kong (CN)

( * ) Notice: Subject to any disclaimer, the term of this patent is extended or adjusted under 35 U.S.C. 154(b) by 509 days.

(21) Appl. No.: 12/660,885

(22) Filed: Mar. 5, 2010

(65) Prior Publication Data

US 2010/0167356 A1 Jul. 1, 2010

Related U.S. Application Data

(63) Continuation of application No. 12/584,684, filed on Sep. 10, 2009, now abandoned.

(60) Provisional application No. 61/095,877, filed on Sep. 10, 2008.

(51) Int. Cl.
*C12N 15/64* (2006.01)
*C12N 15/70* (2006.01)

(52) U.S. Cl.
USPC ...................... 435/471; 435/320.1

(58) Field of Classification Search
None
See application file for complete search history.

(56) References Cited

U.S. PATENT DOCUMENTS

| 5,518,900 A | 5/1996 | Nikiforov et al. |
|---|---|---|
| 2002/0102655 A1 | 8/2002 | Laible et al. |
| 2003/0036198 A1 | 2/2003 | Stewart et al. |
| 2003/0162265 A1 | 8/2003 | Evans et al. |
| 2005/0130159 A1 | 6/2005 | Rigler et al. |
| 2005/0164213 A1 | 7/2005 | Tabor et al. |
| 2006/0024698 A1 | 2/2006 | Cox et al. |
| 2007/0037196 A1 | 2/2007 | Gibson et al. |

OTHER PUBLICATIONS

Int'l Search Report and Written Opinion issued on Dec. 28, 2009 in Int'l Application No. PCT/US09/56510.
Liu et al; A Highly Efficient Recombineering-Based Method for Generating Conditional Knockout Mutations; Genome Research; 13; (2003) pp. 476-484.
In-Fusion Dry-Down PCR Cloning Kit User Manual; Clontech Laboratories, Inc.; Aug. 2009; 19 pages.
International Preliminary Report on Patentability, dated Mar. 24, 2011, in counterpart International Application No. PCT/US2009/056510.
Office Action issued Jul. 13, 2012 in U.S. Appl. No. 13/362,382.
Office Action issued Feb. 1, 2013 in U.S. Appl. No. 13/362,382.

*Primary Examiner* — Nancy T Vogel
(74) *Attorney, Agent, or Firm* — Panitch Schwarze Belisario & Nadel LLP

(57) ABSTRACT

Methods and compositions for cloning a donor DNA molecule into an acceptor vector at a predetermined location are described. The methods are based on homologous recombination mediated by in vitro treatment of the donor DNA and the acceptor vector with an enzyme cocktail containing an exonuclease and a single-stranded DNA binding protein.

13 Claims, 1 Drawing Sheet
(1 of 1 Drawing Sheet(s) Filed in Color)

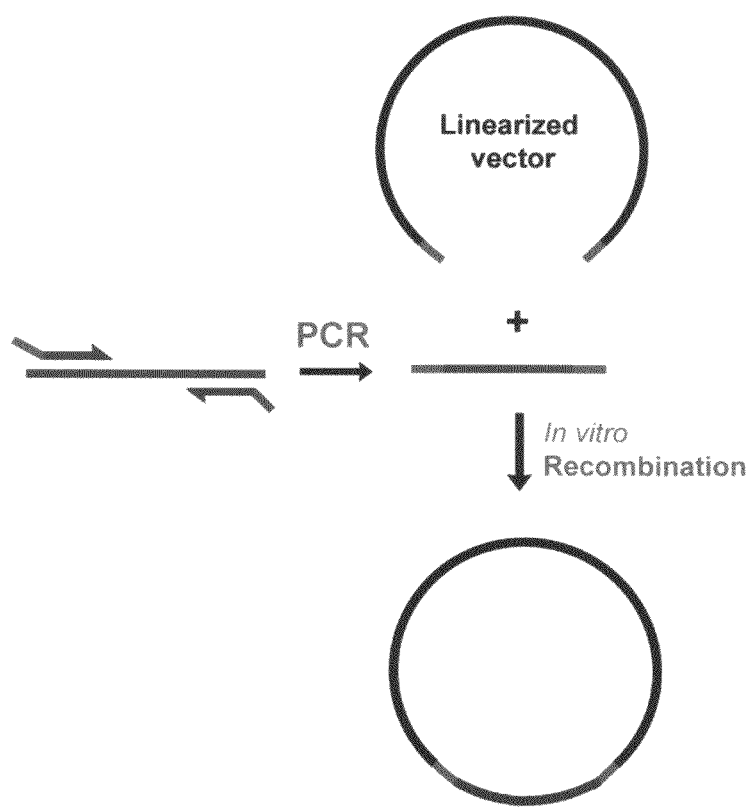

HOMOLOGOUS RECOMBINATION-BASED DNA CLONING METHODS AND COMPOSITIONS

CROSS-REFERENCE TO RELATED APPLICATIONS

This application is a continuation of copending application Ser. No. 12/584,684 filed on Sep. 10, 2009, which is entitled to and claims the benefit of the priority pursuant to 35 U.S.C. §119(e) of U.S. Provisional Patent Application No. 61/095,877, filed Sep. 10, 2008, the disclosure of which is hereby incorporated by reference in its entirety.

BACKGROUND OF THE INVENTION

1. Field of the Invention

Embodiments of the present invention relate to methods and compositions for molecular cloning, particularly, cloning of a donor DNA into an acceptor vector at a predetermined location.

2. Background of the Invention

In molecular biology research and biotechnology industry, there is a constant need of cloning a desired DNA molecule into a vector, preferably at a predetermined location. A conventional method for cloning a donor DNA into an acceptor vector at a predetermined location, such as a plasmid, usually involves six major steps: (i) digesting the acceptor vector DNA with one or two restriction endonucleases and purifying the linearized vector; (ii) treating the linearized vector with Calf Intestinal Phosphatase (CIP) to minimize self-recircularization of the linearized vector without the donor DNA during ligation; (iii) amplifying the donor DNA by a polymerase chain reaction (PCR) using PCR primers that will add to the 5'- and 3'-ends of the amplified donor DNA restriction enzyme recognition site(s) for the one or two restriction endonucleases used to linearize the vector DNA; (iv) digesting the amplified donor DNA with the same restriction endonucleases used to linearize the vector DNA and purifying the digested donor DNA; (v) ligating the purified donor DNA and the purified linearized vector using DNA ligase; and (vi) transforming the ligation products into recipient cells, such as competent *Escherichia coli* cells, and selecting transformants containing the desired cloning product where the donor DNA is inserted in the vector at the desired cloning site. The conventional cloning method is cumbersome and time-consuming. It has relatively low cloning efficiency. It is also limited by the availability of suitable restriction enzyme recognition sites on the vector and the donor DNA.

Recombination-based methods have been used to expedite cloning. For example, a recombineering-based method for generating conditional knockout mutations was described by Pentao Liu, et al. (*Genome Res* (2003) 13: 476-484). The method uses a phage-based *E. coli* homologous recombination system without the need for restriction enzymes or DNA ligases. In particular, the method uses homologous recombination mediated by the λ phage Red proteins, to subclone DNA from bacterial artificial chromosomes (BACs) into high-copy plasmids by gap repair, and together with Cre or Flpe recombinases, to introduce loxP or FRT sites into the subcloned DNA. Longer than 45-55-bp regions of homology are used in the method. Like several other recombination-based methods, the method depends on specific sequences within the acceptor vector and the expression of specific phage proteins in the host cell, thus restricts the user to particular vectors and host cells.

Another example of recombination-based cloning is developed by Clontech Laboratories, Inc. (Mountain View, Calif. 94043), as In-Fusion™ PCR Cloning Kits. The Kits purport to allow cloning of any PCR fragment into any linearized vector in a single step without restriction digestion of the PCR fragment, ligation or blunt-end polishing. The In-Fusion™ system allows to fuse the ends of the PCR fragment to the homologous ends of a linearized vector. The 3' and 5' regions of homology are generated by adding 15 bp extensions to both PCR primers that precisely match the ends of the linearized vector. The method consists of 30 minutes incubation of the linearized vector with the PCR fragment and In-Fusion™ enzyme, followed by transformation of *E. coli*. The In-Fusion™ enzyme is a proprietary protein that converts the double-stranded extensions into single-stranded DNA and fuses these regions to the corresponding ends of the linearized vector. While the In-Fusion™ system does allow rapid directional cloning of PCR product without the restrictions of vectors and host cells, it depends on the proprietary In-Fusion™ enzyme, thus restricts the user to the In-Fusion™ PCR Cloning Kits or similar systems sold by Clontech or its affiliates.

Therefore, there is a need for a novel fast and simple method for cloning a donor DNA in a predetermined location of a vector. Such method is described in the present application. The method according to embodiments of the present invention has all the privileges of the In-Fusion™ PCR Cloning Kits with even higher cloning efficiency using an enzyme cocktail instead of the In-Fusion™ enzyme.

BRIEF SUMMARY OF THE INVENTION

In one general aspect, embodiments of the present invention relate to a method of cloning a donor DNA molecule into an acceptor vector at a predetermined location. The method comprises:

a) preparing an extended donor DNA molecule by adding to the 5'-end and the 3'-end of the donor DNA molecule a first sequence and a second sequence, respectively, wherein each of the first and second sequences, independently, is at least 12 nucleotides in length and is at least 90% identical to a first region and a second region of the acceptor vector, respectively;

b) providing a reaction mixture comprising
   i) the acceptor vector;
   ii) the extended donor DNA molecule; and
   iii) an enzyme cocktail comprising an exonuclease and a single-stranded DNA binding protein;

c) incubating the reaction mixture to obtain an intermediate product;

d) transforming a cell with the intermediate product to obtain a transformed cell; and e) culturing the transformed cell under conditions to produce a recombinant DNA molecule comprising the donor DNA located between the first region and the second region.

In an embodiment according to the present invention, the extended donor DNA is prepared by polymerase chain reaction (PCR).

In another general aspect, embodiments of the present invention relate to a composition for use in cloning a donor DNA molecule into an acceptor vector at a predetermined location. The composition comprises:

a) an enzyme cocktail comprising an exonuclease and a single-stranded DNA binding protein; and b) a reaction buffer.

An embodiment of the present invention also relates to a kit for use in cloning a donor DNA molecule into an acceptor vector at a predetermined location. The kit comprises the composition according to embodiments of the present invention and instructions on using the kit in the cloning.

In yet another general aspect, embodiments of the present invention relate to a system for use in cloning a donor DNA molecule into an acceptor vector at a predetermined location. The system comprises:

a) the acceptor vector;
b) an extended donor DNA molecule comprising a first sequence and a second sequence at the 5'-end and the 3'-end of the donor DNA molecule, respectively, wherein each of the first and second sequences, independently, is at least 12 nucleotides in length and is at least 90% identical to a first region and a second region of the acceptor vector, respectively;
c) an enzyme cocktail comprising an exonuclease and a single-stranded DNA binding protein; and
d) a cell transformable with an intermediate product formed after incubating a reaction mixture comprising (a), (b) and (c), whereby the transformed cell produces a recombinant DNA molecule that comprises the donor DNA located between the first region and the second region.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

The patent or application file contains at least one drawing executed in color. Copies of this patent or patent application publication with color drawing(s) will be provided by the Office upon request and payment of the necessary fee.

In the drawing:

FIG. 1 is a schematic representation of a method according to an embodiment of the present invention.

DETAILED DESCRIPTION OF THE INVENTION

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, "sequence" means the linear order in which monomers occur in a polymer, for example, the order of amino acids in a polypeptide or the order of nucleotides in a polynucleotide.

As used herein, the term "nucleotide sequence", "nucleic acid" or "polynucleotide" refers to the arrangement of either deoxyribonucleotide or ribonucleotide residues in a polymer in either single- or double-stranded form. Nucleic acid sequences can be composed of natural nucleotides of the following bases: T, A, C, G, and U, and/or synthetic analogs of the natural nucleotides. In the context of the present invention, adenosine is abbreviated as "A", cytidine is abbreviated as "C", guanosine is abbreviated as "G", thymidine is abbreviated as "T", and uridine is abbreviated as "U". A polynucleotide can be a single-stranded or a double-stranded nucleic acid. Unless otherwise indicated, a polynucleotide is not defined by length and thus includes very large nucleic acids, as well as short ones, such as an oligonucleotide.

Conventional notation is used herein to describe polynucleotide sequences. The left-hand end of a single-stranded polynucleotide sequence is the 5'-end. The left-hand end of a double-stranded polynucleotide sequence is the 5'-end of the plus strand, which is depicted as the top strand of the double strands, and the right-hand end of the double-stranded polynucleotide sequence is the 5'-end of the minus strand, which is depicted as the bottom strand of the double strands. The direction of 5' to 3' addition of nucleotides to nascent RNA transcripts is referred to as the transcription direction. A DNA strand having the same sequence as an mRNA is referred to as the "coding strand." Sequence on a DNA strand which is located 5' to a reference point on the DNA is referred to as "upstream sequence"; sequence on a DNA strand which is 3' to a reference point on the DNA is referred to as "downstream sequence."

As used herein, a "complement of a nucleotide sequence" is a nucleic acid sequence that is 100% complementary to the nucleotide sequence.

"Sequence identity", as known in the art, is the relationship between two or more polypeptide sequences or two or more polynucleotide sequences, as determined by comparing the sequences. As used herein, "identity", in the context of the relationship between two or more nucleic acid sequences or two or more polypeptide sequences, refers to the percentage of nucleotide or amino acid residues, respectively, that are the same when the sequences are optimally aligned and analyzed. The identity is calculated along with the percentage of identical matches between the two sequences over the reported aligned region, including any gaps in the length. Analysis can be carried out manually or using sequence comparison algorithms. For sequence comparison, typically one sequence acts as a reference sequence, to which a queried sequence is compared. When using a sequence comparison algorithm, test and reference sequences are input into a computer, sub-sequence coordinates are designated, if necessary, and sequence algorithm program parameters are designated.

Optimal alignment of sequences for comparison can be conducted by methods known in the art, such as the homology algorithm of Needleman & Wunsch, *J. Mol. Biol.* 48:443 (1970), Smith & Waterman, *Adv. Appl. Math.* 2:482 (1981) or Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of algorithm that is suitable for determining percent sequence identity and sequence similarity is the BLAST algorithm, which is described in Altschul et al, *J. Mol. Biol.* 215:403-410 (1990). Software for performing BLAST analyses is publicly available online through the National Center for Biotechnology Information (NCBI) web site.

As used herein, "recombinant" refers to a polynucleotide, a polypeptide encoded by a polynucleotide, a cell, a viral particle or an organism that has been modified using molecular biology techniques to something other than its natural state.

As used herein, a "recombinant DNA molecule" refers to a DNA molecule that does not exist as a natural product, but is produced using molecular biology techniques.

As used herein, a "transformed cell", "transfected cell", "transformant" and "recombinant cell" all refer to a cell that has had introduced into it a recombinant polynucleotide sequence. For example, transformed cells can contain at least one nucleotide sequence that is not found within the native (non-transformed) form of the cell or can express native genes that are otherwise abnormally expressed, under-expressed, or not expressed at all. Transformed cells can also contain genes found in the native form of the cell wherein the genes are modified and re-introduced into the cell by artificial means. The term encompasses cells that contain the recombinant polynucleotide sequence either on a vector, or integrated into a cell chromosome.

Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. It is further understood that the term "transformed cell" refers not only to the particular subject cell, but also to the progeny or potential progeny of such a cell. Because certain modifications can occur in succeeding generations due to either mutation or environmental influences, and in such circumstances, such progeny may not, in fact, be identical to the parent cell, but are still included within the scope of the term as used herein.

As used herein, the term "vector" refers to a nucleic acid molecule capable of transporting another nucleic acid to which it has been linked. One type of vector is a plasmid, which refers to a circular double stranded DNA loop into which additional DNA segments can be inserted. Another type of vector is a viral vector, wherein additional DNA segments can be inserted. Other types of vectors include, but are not limited to, bacterial artificial chromosomes (BACs), yeast artificial chromosomes (YACs), and phagemid. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, vectors of utility in recombinant DNA techniques are often in the form of plasmids. These plasmids can be single, low, medium or high copy plasmids. Examples of such vectors are described, for example, by Sambrook et al. (*Molecular Cloning, Laboratory Manual,* 2nd Edition (1989), Cold Spring Harbor Laboratory Press) and Ioannou et al. (*Nature Genet.* 6 (1994), 84-89) or references cited therein. However, the invention is intended to also include other forms of vectors, such as viral vectors (e.g., replication defective retroviruses, adenoviruses and adeno-associated viruses), BACs, YACs, and phagemid, which serve equivalent functions.

Specifically designed vectors allow the cloning of DNA in different hosts or the shuttling of DNA between hosts such as bacteria-yeast or bacteria-animal cells or bacteria-fungal cells or bacteria-invertebrate cells. Numerous vectors are known to those of skill in the art and the selection of an appropriate vector is a matter of choice. For other suitable expression systems for both prokaryotic and eukaryotic cells see chapters 16 and 17 of Sambrook et al. (supra).

Embodiments of the present invention relate to a quick DNA cloning method, which is a significant improvement over the conventional DNA cloning techniques as well as other recombination-based cloning methods. According to embodiments of the present invention, virtually any donor DNA molecule can be cloned into any vector at any predetermined location using a method that no longer requires several steps in the conventional DNA cloning method, such as restriction enzyme digestion of the PCR amplified donor DNA, dephosphorylation of the restriction enzyme digested acceptor vector with alkaline phosphatase, ligation of the donor DNA with the acceptor DNA using DNA ligase, etc. Methods according to embodiments of the invention greatly reduce the time and costs for cloning, while give the user greater flexibility of the vectors and host cells to be used in the cloning. The cloning method according to embodiments of the present invention employs homologous recombination between a donor DNA molecule and an acceptor vector.

In one general aspect of the present invention, a donor DNA molecule can be cloned into an acceptor vector at predetermined location using a method that comprises the following steps:

a) preparing an extended donor DNA molecule by adding to the 5'-end and the 3'-end of the donor DNA molecule a first sequence and a second sequence, respectively, wherein each of the first and second sequences, independently, is at least 12 nucleotides in length and is at least 90% identical to a first region and a second region of the acceptor vector, respectively;

b) providing a reaction mixture comprising
  i) the acceptor vector;
  ii) the extended donor DNA molecule; and
  iii) an enzyme cocktail comprising an exonuclease and a single-stranded DNA binding protein;

c) incubating the reaction mixture to obtain an intermediate product;

d) transforming a cell with the intermediate product to obtain a transformed cell; and e) culturing the transformed cell under conditions to produce a recombinant DNA molecule comprising the donor DNA located between the first region and the second region.

Acceptor Vector

The choice and use of acceptor vectors in the present invention will be readily apparent to those of skill in the art in view of the present disclosure. The acceptor vector can be any vector known in the art, such as a plasmid, a BAC, a YAC, a virus, or a phagemid.

In an embodiment of the present invention, an acceptor vector has an origin of replication sequence that allows autonomous replication of the constructed recombinant DNA inside a transformed prokaryotic or eukaryotic host cell. For example, the acceptor vector can have the ColE1 origin of replication for autonomous replication of the constructed recombinant DNA inside *E. coli* host cells, 2µ origin of replication for yeast host cells, or a virus origin of replication, e.g., SV40 origin of replication, for host cells containing the appropriate replication factors for virus replicons.

In another embodiment of the present invention, an acceptor vector has sequences that facilitate integration or incorporation of the constructed recombinant DNA onto the genome of the transformed cell.

In an embodiment of the present invention, the acceptor vector contains a sequence that allows the constructed recombinant DNA to express a marker gene product that is not expressed by the acceptor vector, thereby allowing selection or screening of transformed cells containing the recombinant DNA by the selection or screening of the presence of the marker gene product. This can be achieved by the design of the recombinant DNA, for example, by providing missing element of the marker gene through insertion of the donor DNA.

In another embodiment of the present invention, the acceptor vector contains a sequence that allows the constructed recombinant DNA to not express a marker gene product that is expressed by the acceptor vector, thereby allowing selection or screening of transformed cells containing the recombinant DNA by the selection or screening of the absence of the marker gene product. This can be achieved by the design of the recombinant DNA, for example, by nullifying the marker gene through insertion of the donor DNA.

The marker gene can be a selectable marker gene, the expression of which allows the selection of the transformed cells on a selective medium. Examples of selectable marker genes include, but are not limited to, those encode proteins that confer resistance to drugs, such as antibiotics, G418, hygromycin and methotrexate; and those that encode proteins that confer the ability to grow in medium lacking what would be an essential nutrient.

The marker gene can also be a reporter gene, the expression of which allows easy screening of the transformed cells using conventional lab techniques. Examples of reporter gene include, but are not limited to, those encode green fluorescent protein (GFP), β-galactosidase, luciferase, chloramphenicol acetyltransferase, β-glucuronidase, neomycin phosphotransferase, guanine xanthine phosphoribosyl-transferase, etc.

A marker gene differently expressed in the acceptor vector and the constructed recombinant DNA would allow easy selection or screening of transformed cells containing the recombinant DNA from those containing the acceptor vector only. However, such a feature may be present, but is not required, for a method according to the present invention, because of the high cloning efficiency provided by the present method. Transformants containing the recombinant DNA can be easily identified by PCR screening using methods known in the art in view of the present disclosure.

The donor DNA can be cloned into an acceptor vector at any predetermined location.

The cloning location can be chosen according to the experimental need. The donor DNA can be inserted into the acceptor vector with or without replacing or deleting a portion of the vector. If a portion of an autonomously replicating acceptor vector is deleted as a result of the homologous recombination, care is taken to ensure that the origin of replication of the vector remains in the constructed recombinant DNA.

Once a location for insertion of the donor DNA molecule is chosen, sequences of the two regions flanking the chosen location on the acceptor vector are readily discernable, e.g., by pre-existing sequence of the vector or by DNA sequencing of the regions.

As used herein, the "first region" refers to the sequence located upstream of the 5'-end of the predetermined insertion site. When precise insertion of the donor DNA at the 5'-end of the insertion site is required, the first region is contiguous with the first or 5' most nucleotide of the predetermined insertion location.

As used herein, the "second region" refers to the sequence located downstream of the 3'-end of the predetermined insertion site. When precise insertion of the donor DNA at the 3'-end of the insertion site is required, the second region is contiguous with the last or 3' most nucleotide of the predetermined insertion location.

In an embodiment of the present invention, the acceptor vector is a plasmid, and the predetermined location for the insertion of the donor DNA is at a restriction endonuclease cleavage site, or is between two restriction endonuclease cleavage sites. The plasmid is digested with the one or, two restriction endonucleases. After the restriction enzyme digestion, the one or two restriction enzymes are heat-inactivated, and the linearized plasmid is purified by gel or column purification. The first region and the second region are the sequences at the two ends of the linearized plasmid, respectively.

In another embodiment of the present invention, the acceptor vector is circular, undigested or uncut with any restriction enzyme. An uncut plasmid can be used directly in a reaction mixture for homologous recombination according to an embodiment of the present invention.

Preparation of the Extended Donor DNA Molecule

Any donor DNA can be cloned into a vector using the present invention. Examples of donor DNA molecules include, without limitation, cDNA or genomic DNA fragments. The donor DNA molecule can be a gene encoding a protein of interest. It can also be a sequence carrying a genetic mutation or genetic lesion of interest, for performing quick DNA mutagenesis. The genetic mutations or genetic lesions include, but are not limited to: 1) a deletion of one or more nucleotides from a target DNA; 2) an addition of one or more nucleotides to the target DNA; 3) a substitution of one or more nucleotides of the target DNA; etc. DNA mutagenesis, e.g., introducing DNA mutations including point mutations, additions and deletions, is traditionally performed in the same way as DNA cloning using conventional methods. The method of the present invention can also be used for quick DNA mutagenesis, thereby significantly reducing the time and associated costs for DNA mutagenesis.

In an embodiment of the present invention, the donor DNA is extended by adding to each of its two ends a first sequence or a second sequence that shares sufficient homology with the first region or the second region of the acceptor vector described supra, so that efficient homologous recombination occurs precisely between the first sequence and first region, and the second sequence and the second region, respectively.

In another embodiment of the present invention, each of the first and second sequences, independently, is at least 12 nucleotides in length and shares at least about 90% sequence identity to the first and second regions, respectively. For example, each of the first and second sequences, independently, can be 12, 15, 20, 25, 30, 35, 40, 45, 50 nucleotides in length and share about 90%, 95% or 100% sequence identity with the first and second regions, respectively.

In an embodiment of the present invention, each of the first and second sequences, independently, is at least 12 nucleotides in length and shares about 100% sequence identity to the first and second regions, respectively.

The extended donor DNA molecule can be prepared using any method known in the art in view of the present disclosure. For example, the extended donor DNA can be synthesized by chemical synthesis. The extended DNA can also be recombinantly produced followed by appropriate restriction enzyme cleavage and purification.

In a preferred embodiment, the extended donor DNA molecule is produced by PCR. Each of the PCR primers is composed of two parts: a 5'-end add-on sequence and 3'-end donor DNA specific sequence. One of the PCR primers contains the first sequence as the 5'-end add-on sequence and the other primer contains the complement of the second sequence. Methods known in the art can be used to design the 3'-end donor DNA specific sequences in the PCR primers in view of the present disclosure. For example, the donor DNA specific sequences must be specific to the targeted regions on the donor DNA, can be 10-25 bases in length and have a GC content of about 35-65%. Preferably, the two PCR primers have similar melting temperature ($T_m$) in the range of 55-70° C., etc.

Any of the PCR applications known in the art can be used in view of the present disclosure. PCR conditions, such as the amounts of template and primers, the concentrations of $Mg^{2+}$ and dNTPs, the annealing and thermocycling conditions, etc., can be chosen or optimized by common knowledge or routine experimentation.

In an embodiment of the present invention, more than one donor DNA molecules can be cloned in a desired order at a predetermined location on an acceptor vector. The add-on sequences at the ends of the extended donor DNA molecules are designed such to allow homologous recombination between the donor DNA molecules in the desired order, as well as to allow homologous recombination between the donor DNA molecules and the acceptor vector at the predetermined location.

Alternatively, more than one donor DNA molecules can first be joined together using methods known in the art, such as by DNA ligation or by fusion PCR. The joint product containing multiple donor DNA molecules can then be inserted into the acceptor vector using methods of the present invention.

In another embodiment of the present invention, a group of donor DNA molecules of heterogeneous sequences, e.g. from a DNA library or cDNA library, can be cloned at a predetermined location on an acceptor vector. For example, a pair of universal PCR primers can be used to add the first and the second sequences to the ends of each of the donor DNA molecules via PCR. The extended heterogeneous donor DNA sequences are then cloned onto the acceptor vector through homologous recombination using methods described herein.

Enzyme Cocktail

Unlike the In-Fusion™ Cloning System from Clontech, which uses a proprietary In-Fusion Enzyme, a protein that fuses PCR-generated donor sequence to linearized vectors by recognizing a 15 bp overlap at their ends, methods of the present invention utilize an enzyme cocktail in an in vitro treatment of the extended donor DNA and acceptor vector to initiate and mediate the homologous recombination, which is completed by the recombination system of the transformed cell in vivo.

The enzyme cocktail according to embodiments of the present invention comprises an exonuclease and a single-stranded DNA binding protein. Each of the proteins can be substituted with similar proteins known in the art that function in substantially the same way.

As used herein, the term "exonuclease" refers to an enzyme that cleaves nucleotides one at a time from the end of a polynucleotide chain via a hydrolyzing reaction that breaks phosphodiester bonds at either the 3' or 5' end. The "exonuclease" can be a 3' to 5' exonuclease or a 5' to 3' exonuclease. *E. coli* exonuclease I and exonuclease III are two commonly used 3'-exonucleases that have 3'-exonucleolytic single-strand degradation activity. *E. coli* exonuclease VII and T7-exonuclease Gene 6 are two commonly used 5'-3' exonucleases that have 5% exonucleolytic single-strand degradation activity.

The exonuclease can be originated from prokaryotes, such as *E. coli* exonucleases, or eukaryotes, such as yeast, worm, murine, or human exonucleases.

Examples of exonuclease that can be used in the present invention include, but are not limited to, *E. coli* exonuclease I, *E. coli* exonuclease III, *E. coli* exonuclease VII, bacteriophage lambda exonuclease, and bacteriophage T7-exonuclease Gene 6, or a combination thereof.

As used herein, a "single-stranded DNA binding protein," also known as SSB or SSBP, refers to a protein that binds single stranded regions of DNA. "SSBs" can be originated from viruses to humans. "SSBs" can be monomeric, such as many identified in phage and virus, or multimeric, such as the tetrameric bacterial SSBs or the heterotrimeric eukaryotic Replication Protein A (RPA).

Examples of single-stranded DNA binding proteins that can be used in the present invention include, but are not limited to, extreme thermostable single-stranded DNA binding protein (ET SSB), RecA (such as *E. coli* RecA, any RecA recombinantly expressed by *E. coli*, or derivatives thereof), T4 Gene 32 Protein, *Thermus thermophilus* RecA (Tth RecA), and *E. coli* single-strand DNA binding protein, or a combination thereof.

The enzyme cocktail according to embodiments of the present invention can comprise any of the combination of an exonuclease and an SSB. Examples of such combination, include, but are not limited to, a combination selected from the group consisting of *Escherichia coli* exonuclease I and RecA; *Escherichia coli* exonuclease III and RecA; *Escherichia coli* exonuclease VII and RecA; bacteriophage lambda exonuclease and RecA; bacteriophage T7-exonuclease Gene 6 III and RecA; *Escherichia coli* exonuclease I and Tth RecA; *Escherichia coli* exonuclease III and Tth RecA; *Escherichia coli* exonuclease VII and Tth RecA; bacteriophage lambda exonuclease and Tth RecA; bacteriophage T7-exonuclease Gene 6 III and Tth RecA; *Escherichia coli* exonuclease I and ET SSB; *Escherichia coli* exonuclease I and T4 Gene 32 Protein; *Escherichia coli* exonuclease I and *Escherichia coli* SSB; *Escherichia coli* exonuclease III and ET SSB; *Escherichia coli* exonuclease III and T4 Gene 32 Protein; *Escherichia coli* exonuclease III and *Escherichia coli* SSB; *Escherichia coli* exonuclease VII and ET SSB; *Escherichia coli* exonuclease VII and T4 Gene 32 Protein; and *Escherichia coli* exonuclease VII and *Escherichia coli* SSB.

In Vitro Treatment

According to embodiments of the present invention, the homologous recombination between the extended donor DNA and the acceptor vector is initiated, mediated or facilitated by incubating the DNA molecules and the enzyme cocktail in a reaction mixture in vitro.

The reaction mixture comprises an acceptor vector, an extended donor molecule, an enzyme cocktail, and a reaction buffer.

The reaction buffer comprises buffering agents, salts and adenosine-5'-triphosphate (ATP), having a pH of about 5.0 to about 9.0. In an embodiment of the invention, the reaction buffer comprises tris(hydroxymethyl)aminomethane (Tris), NaCl, EDTA, $MgCl_2$, glycerol, bovine serum albumin (BSA), ATP, and dithiothreitol (DTT), at a pH of about 6.8 to about 7.4. Each of these elements can be substituted with similar elements known in the art that function in solution in substantially the same way. BSA, for example can be substituted with casein and/or other agents known in the art. NaCl can also be replaced by KCl.

In another general aspect, embodiments of the present invention relate to a composition for use in cloning a donor DNA molecule into an acceptor vector at a predetermined location. The composition comprises: a) an enzyme cocktail comprising an exonuclease and a single-stranded DNA binding protein; and b) a reaction buffer.

The enzyme cocktail and the reaction buffer can be provided in a kit for use in cloning a donor DNA molecule into an acceptor vector at a predetermined location, which also includes instructions on using the enzyme cocktail and reaction buffer in the cloning. The kit may further contain a competent cell for use in transformation in the cloning. The kit may also include control vectors or DNA molecules for the cloning.

The enzyme cocktail and reaction buffer can be provided in various forms suitable for their applications. For example, the enzyme cocktail can be provided in a concentrated liquid form or lyophilized form, with or without the accompanying dilution or reconstitution buffer. The reaction buffer can be provided in a single container in a concentrated or lyophilized form. Alternatively, one or more ingredients of the reaction buffer can be provided in separate containers that can be combined together upon use.

In an embodiment of the present invention, the reaction mixture comprises about 0.5 to about 10 ng/µl of the acceptor vector. The reaction mixture can contain, for example, about 0.5, 1, 5 or 10 ng/µl of the acceptor vector.

In an embodiment of the present invention, the reaction mixture comprises about 1 to about 30 ng/µl of the extended DNA molecules. The reaction mixture can contain, for example, about 1, 5, 10, 15, 20, 25 or 30 ng/µl of the extended DNA molecules.

In an embodiment of the present invention, the reaction mixture comprises about 1 to about 100 mg/l of the single-stranded DNA binding protein. The reaction mixture can contain, for example, about 1, 5, 15, 25, 35, 45, 55, 65, 75, 85, 95, or 100 mg/l of the single-stranded DNA binding protein.

In an embodiment of the present invention, the reaction mixture comprises about 1 to about 100 mg/l of the exonuclease. The reaction mixture can contain, for example, about 1, 5, 15, 25, 35, 45, 55, 65, 75, 85, 95, or 100 mg/l of the exonuclease.

In one embodiment of the present invention, 1 liter of the reaction mixture contains about 1 gram to 10 grams, such as about 5 grams, of Tris; about 0.1 gram to 10 grams, such as about 5 grams, of NaCl; about 0.1 grams to about 10 grams, such as about 2 grams, of EDTA; about 0.1 grams to about 10 grams, such as about 1 gram, of $MgCl_2$; about 10 grams to about 200 grams, such as about 50 grams, of glycerol; about 10 grams to 50 grams, such as about 20 grams, of BSA; about 0.1 gram to about 10 grams, such as about 1 gram, of ATP; about 0.1 gram to about 10 grams, such as about 1 gram, of DDT; about 1 miligram to about 100 miligrams, such as 75 miligrams, of RecA (e.g., *E. coli* RecA, any RecA recombinantly expressed by *E. coli*, or derivatives thereof); about 1 miligram to about 100 miligrams, such as about 35 miligrams of *E. coli* Exonuclease VII. The reaction mixture further comprises about 0.5 ng/µl to about 10 ng/µl, such as 5 ng/µl, of the linearized vector; and about 1 ng/µl to about 30 ng/µl, such as about 5 to about 15 ng/µl, of the extended donor DNA. The pH of the reaction mixture can be about 5.0 to about 9.0, such as about 6.8 to about 7.4, or about 7.6.

In an embodiment of the present invention, the reaction mixture is incubated at a temperature of about 10 to 38° C. for about 10 to 60 minutes.

In another embodiment of the present invention, the reaction mixture is incubated at room temperature for about 30 minutes.

It is noted that the present invention is not limited to the concentrations, ingredients, or assay conditions described herein. Equivalent concentrations, ingredients, or assay conditions can also be used.

Transformation

An intermediate product is formed after the in vitro incubation of the reaction mixture. The intermediate product is transformed into a host cell using methods known in the art in view of the present disclosure.

The intermediate product can be introduced into prokaryotic or eukaryotic cells via conventional transformation or transfection techniques, including, but not limited to, calcium phosphate or calcium chloride co-precipitation, electroporation, DEAE-dextran-mediated transfection, lipofection, protoplast fusion, and viral infection. Suitable methods for transforming or transfecting host cells can be found in Sambrook et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

Cells suitable for the transformation of the present invention include, but are not limited to, a bacterial cell, e.g. a Gram-negative bacterial cell, or a Gram-positive bacterial cell, a yeast cell, a mammalian cell, etc.

In an embodiment of the present invention, the cell used for transformation is a competent *E. coli* cell. For example, about 2-10 µl of the reaction mixture after the incubation was used to transform 50 µl of competent cells following standard transformation procedure.

The transformed cells can be selected on a selective medium. Cells containing the recombinant DNA that comprises the donor DNA inserted at the predetermined location of the acceptor vector can be screened using a PCR screening method.

While not wishing to be bound by theory, it is believed that in a method according to an embodiment of the present invention, the homologous recombination is initiated and mediated during in vitro treatment of the acceptor vector and the donor DNA, and is completed in vivo in a transformed cell. It is believed that during the in vitro treatment, the exonuclease acts on the ends on the linear extended donor DNA molecule to produce single-stranded DNA (ssDNA) overhangs at both ends. The SSB binds to the ssDNA overhangs to protect them from degradation, particularly upon introduction into a host cell, such as *E. coli*. It is believed that in the intermediate product formed after the in vitro treatment, the ssDNA overhangs form base pair interactions with their complementary sequences in the first or second regions of the acceptor vector. Upon introduction of the intermediate product into a host cell, the homologous recombination occurs between the first region and first sequence and the second region and the second sequence, respectively, as a result of the recombination functions of the host cell.

Regardless of the underline mechanism, it was found that using methods according to the present invention, donor DNA molecules of different sizes were cloned into vectors at predetermined locations at high efficiency.

Table 1 summarizes the cloning results of donor DNA molecules of the sizes of 1 kb, 2 kb, and 3 kb into UC57 vector.

TABLE 1

|  | PCR DNA Size | | |
| --- | --- | --- | --- |
|  | 1 kb | 2 kb | 4 kb |
| Number of Colonies | ~1200 | ~1000 | 221 |
| Positive Ratio | 8/8 | 7/8 | 7/8 |

In each recombination test, 8 colonies were screened for the correct insertion of the PCR DNA.

In another general aspect, embodiments of the present invention relate to a system for use in cloning a donor DNA molecule into an acceptor vector at a predetermined location. The system comprises:

a) the acceptor vector;

b) an extended donor DNA molecule comprising a first sequence and a second sequence at the 5'-end and the 3'-end of the donor DNA molecule, respectively, wherein each of the first and second sequences, independently, is at least 12 nucleotides in length and is at least 90% identical to a first region and a second region of the acceptor vector, respectively;

c) an enzyme cocktail comprising an exonuclease and a single-stranded DNA binding protein; and d) a cell transformable with an intermediate product formed after incubating a reaction mixture comprising (a), (b) and (c), the transformed cell producing a recombinant DNA molecule that comprises the donor DNA located between the first and the second regions.

Various embodiments of the invention have now been described. It is to be noted, however, that this description of these specific embodiments is merely illustrative of the principles underlying the inventive concept. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES

Hall, D. S. et al., "Homologous pairing and strand exchange promoted by the *Escherichia coli* RecT protein", PNAS USA, vol. 91, pp. 3205-3209 (1994).

Oliner et al., "In vivo cloning of PCR Products in *E. coli*", Nucleic Acids Research, vol 21. No. 22, 1993, pp. 5192-5197.

Nussbaum et al., "Restriction-stimulated recombination of plasmids by the RecE pathway of *Escherichia coli*", Genetics, vol. 130, No. 1, January 1992, pp. 37-49.

Zhang et al., "A new logic for DNA engineering using recombination in *Escherichia coli*", Nature Genetics, vol. 20, No. 2, October 1998, pp. 123-128.

Kolodner et al., "Homologous pairing proteins encoded by the *Escherichia coli* recE and recT genes" Molecular Microbiology, vol. 11, No. 1. 1994. pp. 23-30.

Luisi-Deluca et al., "Genetic and physical analysis of plasmid recombination in recB recC scbB and recB reC scbA *Escherichia coli* K-12 mutants", Genetics, vol. 122, 19889, pp. 269-278.

Degryse et al, "Evaluation of *Escherichia coli* recBC sbcBC mutants for cloning by recombination in vivo", Journal of Biotechnology, vol. 2, No. 39, Apr. 15, 1995, pp. 181-187.

Yang et al., "Homologous recombination based modification in *Escherichia coli* and germ line transmission in transgenic mice of a bacterial artificial chromosome", Nature Biotechnology, vol. 15, September 1997, pp. 859-865.

Murphy, "Lambda Gam protein inhibits the helicase and Chi-stimulated recombination activities of *Escherichia coli* RecBD enzyme", Journal of Bacteriology, vol. 173, No. 18, September 1991, pp. 5808-5821.

We claim:

1. A method of cloning a donor DNA molecule into an acceptor vector at a predetermined location, the method comprising:
   a) preparing an extended donor DNA molecule by adding to the 5'-end and the 3'-end of the donor DNA molecule a first sequence and a second sequence, respectively, wherein each of the first and second sequences, independently, is at least 12 nucleotides in length and is at least 90% identical to a first region and a second region of the acceptor vector, respectively;
   b) providing a reaction mixture comprising:
      i) the acceptor vector;
      ii) the extended donor DNA molecule; and
      iii) an enzyme cocktail comprising an exonuclease having only 3'- or 5'-exonucleolytic single-strand degradation activity, and a single-stranded DNA binding protein;
   c) incubating the reaction mixture to obtain an intermediate product;
   d) transforming a cell with the intermediate product to obtain a transformed cell; and
   e) culturing the transformed cell under conditions to produce a recombinant DNA molecule comprising the donor DNA located between the first region and the second region.

2. The method according to claim 1, wherein the acceptor vector is a circular vector or a linearized vector.

3. The method according to claim 2, wherein the first region and the second region are present at the 3'-end and the 5-end of the linearized vector, respectively.

4. The method according to claim 1, wherein the first and the second sequences are 100% identical to the first and the second regions, respectively.

5. The method according to claim 1, wherein the extended donor DNA molecule is prepared by a polymerase chain reaction (PCR), using a first PCR primer comprising the first sequence and a second PCR primer comprising the complement of the second sequence.

6. The method according to claim 1, wherein the exonuclease is selected from the group consisting of *Escherichia coli* exonuclease I, *Escherichia coli* exonuclease III, *Escherichia coli* exonuclease VII, bacteriophage lambda exonuclease, and bacteriophage T7-exonuclease Gene 6, or a combination thereof.

7. The method according to claim 1, wherein the single-stranded DNA binding protein is selected from the group consisting of extreme thermostable single-strand DNA binding protein (ET SSB), RecA, T4 Gene 32 Protein, *Thermus thermophilus* RecA (Tth RecA) and *Escherichia coli* single-strand DNA binding protein (SSB), or a combination thereof.

8. The method according to claim 7, wherein the enzyme cocktail comprises a combination selected from the group consisting of *Escherichia coli* exonuclease I and RecA; *Escherichia coli* exonuclease III and RecA; *Escherichia coli* exonuclease VII and RecA; bacteriophage lambda exonuclease and RecA; bacteriophage T7-exonuclease Gene 6 III and RecA; *Escherichia coli* exonuclease I and Tth RecA; *Escherichia coli* exonuclease III and Tth RecA; *Escherichia coli* exonuclease VII and Tth RecA; bacteriophage lambda exonuclease and Tth RecA; bacteriophage T7-exonuclease Gene 6 III and Tth RecA; *Escherichia coli* exonuclease I and ET SSB; *Escherichia coli* exonuclease I and T4 Gene 32 Protein; *Escherichia coli* exonuclease I and *Escherichia coli* SSB; *Escherichia coli* exonuclease III and ET SSB; *Escherichia coli* exonuclease III and T4 Gene 32 Protein; *Escherichia coli* exonuclease III and *Escherichia coli* SSB; *Escherichia coli* exonuclease VII and ET SSB; *Escherichia coli* exonuclease VII and T4 Gene 32 Protein; and *Escherichia coli* exonuclease VII and *Escherichia coli* SSB.

9. The method according to claim 1, wherein the reaction mixture comprises about 1 to about 100 mg/l of the exonuclease and about 1 to about 100 mg/l of the single-stranded DNA binding protein.

10. The method according to claim 1, wherein the reaction mixture further comprises about 1 to about 10 g/l of tris (hydroxymethyl)aminomethane (Tris), about 0.1 to about 10 g/l of NaCl, about 0.1 to about 10 g/l of ethylenediaminetetraacetic acid (EDTA), about 0.1 to about 10 g/l of $MgCl_2$, about 10 to about 200 g/l of glycerol, about 10 to about 50 g/l of bovine serum albumin (BSA), about 0.1 to about 10 g/l of adenosine-5'-triphosphate (ATP), about 0.1 to about 10 g/l of dithiothreitol (DTT), and wherein the pH of the reaction mixture is about 5.0 to about 9.0.

11. The method according to claim 1, wherein in step (c), the incubation is conducted at a temperature of about 10° C. to about 38° C. for about 15 minutes to about 60 minutes.

12. The method according to claim 1, wherein the cell is an *Escherichia coli* cell and the acceptor vector is a plasmid comprising an origin of replication that directs replication of the plasmid in the *Escherichia coli* cell.

13. The method according to claim 1, wherein the transformed cell expresses a marker gene from the recombinant DNA molecule that allows the selection or screening of the transformed cell.

\* \* \* \* \*